United States Patent [19]

Rosback et al.

[11] 4,036,744

[45] July 19, 1977

[54] OLEFIN SEPARATION PROCESS

[75] Inventors: Donald H. Rosback, Elmhurst; Richard W. Neuzil, Downers Grove, both of Ill.

[73] Assignee: UOP Inc., Des Plaines, Ill.

[21] Appl. No.: 599,918

[22] Filed: July 28, 1975

Related U.S. Application Data

[60] Continuation-in-part of Ser. No. 531,656, Dec. 11, 1974, Pat. No. 3,969,223, which is a continuation-in-part of Ser. No. 423,599, Dec. 10, 1973, abandoned, which is a division of Ser. No. 317,861, Dec. 22, 1972, Pat. No. 3,929,669.

[51] Int. Cl.$^2$ .................. C10G 25/04; B01J 29/08
[52] U.S. Cl. .................. 208/310 Z; 260/677 AD
[58] Field of Search ............ 208/310 Z; 260/676 MS, 260/677 AD; 252/455 Z

[56] References Cited

U.S. PATENT DOCUMENTS

| | | | |
|---|---|---|---|
| 3,331,882 | 7/1967 | Mattox | 208/310 Z |
| 3,374,182 | 3/1968 | Young | 252/455 Z |
| 3,549,558 | 12/1970 | Berry et al. | 252/455 Z |
| 3,717,572 | 2/1973 | Gramont et al. | 208/310 Z |

*Primary Examiner*—Herbert Levine
*Attorney, Agent, or Firm*—James R. Hoatson, Jr.; Thomas K. McBride; William H. Page, II

[57] ABSTRACT

An improved process for the separation of olefins from a hydrocarbon feed mixture comprising olefins and saturates which process uses an adsorbent comprising sodium type X or sodium type Y zeolite to selectively adsorb the olefins. The improvement comprises employing an adsorbent produced by the steps of: contacting a precursor mass comprising type X or type Y zeolite having a $Na_2O/Al_2O_3$ ratio less than about 0.7 with an aqueous sodium hydroxide solution at ion exchange conditions to effect the addition of sodium cations to the mass and the removal of a small amount of silica and alumina, washing the mass with water to remove excess sodium hydroxide solution; and, at least partially dehydrating the mass at dehydrating conditions thereby producing an adsorbent which has both increased capacity for olefins and decreased catalytic activity.

10 Claims, No Drawings

OLEFIN SEPARATION PROCESS

CROSS-REFERENCE TO RELATED APPLICATIONS

This application is a continuation-in-part application of our copending application Ser. No. 531,656 filed on Dec. 11, 1974, now U.S. Pat. No. 3,969,223, July 13, 1976 which is a continuation-in-part application of application Ser. No. 423,599 filed on Dec. 10, 1973, and abandoned on Jan. 8, 1975, which is a division of copending application Ser. No. 317,861 filed on Dec. 22, 1972, now U.S. Pat. No. 3,929,669, Dec. 30, 1975. The teachings of said copending continuation-in-part application are incorporated herein by specific reference thereto.

BACKGROUND OF THE INVENTION

1. Field of the Invention

The field of art to which this invention pertains is hydrocarbon separation. More specifically, this invention relates to a process for separating olefins from a hydrocarbon feed mixture containing olefins and saturates which process employs a zeolitic adsorbent.

2. Description of the Prior Art

The treating of zeolites with certain substances to modify certain of these properties when used in various separation processes has been recognized by the prior art. U.S. Pat. No. 3,106,593 for instance teaches the use of nitrogen-containing bases such as ammonia and various amines to neutralize surface acidity of certain zeolites used to separate olefins; U.S. Pat. No. 3,698,157 teaches that contacting ZSM-5 and ZSM-8 zeolites with organic-radical substituted silanes improves the selectivity of the zeolites for para-xylene with respect to the other xylenes when used in a xylene separation process; U.S. Pat. No. 3,855,333 teaches that contacting X or Y zeolites with certain alcohols improves the selectivity of the zeolite for the para-isomer with respect to other isomers when used in a para-isomer separation process. More specifically, the prior art has also recognized that treating certain zeolites with caustic solutions will modify particular zeolite properties and produce certain results depending on the type of zeolite and the treating conditions employed.

U.S. Pat. No. 3,326,797, for example, discloses treating high-silica zeolites, having silica to alumina mole ratios between about 6 and 12 (for example, mordenite) with caustic solutions for the purpose of removing a certain percentage of structural silica from the zeolites. The caustic treatment of such a high-silica zeolite, at conditions to preferably retain a final $SiO_2/Al_2O_3$ ratio greater than about 5.5, is found to increase the adsorptive capacity of the zeolite and to increase its catalytic activity particularly when used as a catalyst in such acid-catalyzed reactions such as cracking. The caustic treating of this patent is concerned with etching or leaching of silica from the particular zeolite structure to achieve these characteristics and does not disclose or suggest the addition of alkali metal cations to the zeolite structure during the treating process.

U.S. Pat. No. 3,717,572 discloses treating A zeolites with nitrogen-free base solutions to modify "surface acidity" of the zeolite when used in a process for separating straight-chain olefins from branch-chain olefins. In contrast to the high-silica zeolites of U.S. Pat. No. 3,326,797, the type A zeolite is characterized by a rather low silica to alumina mole ratio, as taught in U.S. Pat. No. 2,882,243, within the range of 1.85±0.5. The treatment of such zeolites appears to be merely an acid-base reaction to neutralize surface acidity; the base appears not critical and can be generally bases whose cation is an alkaline metal, for instance, soda, potash, and lithium hydroxide. Treatment conditions are such that the concentration of the base solution after impregnation is about the same as the fresh base solution. The result desired and that produced with the particular zeolite is only neutralization of acidity; indeed, the preferred solvent for the base solution is an organic medium (in particular methanol) since in such cases neutralization is obtained while maintaining a practically unchanged adsorptive capacity of the sieve. Neutralization by aqueous base solutions actually lowers this capacity.

Thus the prior art has recognized that similar base treatments of different zeolites can produce different results. Such is not surprising since the zeolites vary considerably in such chemical and physical properties as composition, silica to alumina mole ratio, symmetry, cell dimensions, structure, density, pore diameter, and surface area.

The process of our invention employs an adsorbent comprising sodium type X or sodium type Y zeolite prepared by a method which includes a treatment step of a precursor mass comprising type X or Y zeolite with an aqueous caustic solution. We have found that the treatment of such precursor mass at particular treatment conditions will produce an adsorbent having increased capacity for olefins and decreased catalytic activity when used in a process for separating olefins from paraffins. We have found that catalytic activity of the finished adsorbent decreases in proportion to the amount of sodium cations added to the zeolite by the caustic treatment. Specifically, we have found that a sodium content, expressed as the ratio $Na_2O/Al_2O_3$, above about 0.7 is required to produce an adsorbent having the desired properties. The sodium cation added by the ion-exchange apparently replaces acid sites within the zeolite that catalyze isomerization and polymerization reaction. The removal of a small amount of silica and alumina from the precursor mass results in improved capacity of the adsorbent for olefins.

Employing the adsorbent so produced in an olefin separation process results in an improved olefin separation process because less adsorbent is required due to the adsorbent's increased capacity and because the adsorbent has a larger effective on-stream life due to its reduced catalytic activity.

SUMMARY OF THE INVENTION

It is, accordingly, a broad object of our invention to provide an improved process for separating olefins from a feed mixture comprising olefins and saturates wherein the improvement comprises employing an adsorbent superior to those employed in prior art processes.

In brief summary our invention is, in one embodiment, an improved process for the separation of olefins from a feed mixture comprising olefins and saturates, which process comprises the steps of: (a) contacting at adsorption conditions said mixture with an adsorbent comprising sodium type X or sodium type Y zeolite; and (b) selectively adsorbing said olefins to the substantial exclusion of said saturates and thereafter recovering said olefins, the improvement which comprises employing an adsorbent prepared by the steps of: (i) contacting a precursor mass comprising type X or type Y zeolite having a $Na_2O/Al_2O_3$ ratio less than about 0.7 with an aqueous sodium hydroxide solution at ion exchange conditions to increase the sodium cation content to a $Na_2O/Al_2O_3$ ratio of greater than about 0.7 and to remove from about 1 to about 15 wt. % silica and alumina from the precursor mass; (ii) washing said mass with water maintained at pH greater than 7 to remove excess sodium hydroxide solution and, (iii) at least partially dehydrating said mass at dehydrating conditions.

Other embodiments and objects of the present invention encompass details about feed mixtures, adsorbents, desorbents, and operating conditions all of which are hereinafter disclosed in the following discussion of each of these facets of the present invention.

DESCRIPTION OF THE INVENTION

Charge stocks which may be used in the above or other selective adsorption separation processes may contain olefins in the $C_4$–$C_{20}$ carbon range. Of these olefins, those in the $C_{10}$–$C_{15}$ range are particularly preferred. The $C_{10}$–$C_{15}$ normal mono-olefins are generally produced by catalytically dehydrogenating a $C_{10}$–$C_{15}$ normal paraffin stream. The effluent stream from a dehydrogenation process generally contains about 5 to 25% olefins and may require further processing in order to concentrate the normal olefinic hydrocarbons.

A typical example of the composition of the effluent stream from a dehydrogenation process is shown below in Table 1.

TABLE 1

DEHYDROGENATION REACTOR EFFLUENT ANALYSIS BY GAS-LIQUID CHROMATOGRAPHY

|  |  | Wt. % |
|---|---|---|
| n-$C_{10}$ paraffin |  | 0.1 |
| n-$C_{11}$ paraffin |  | 24.9 |
| n-$C_{11}$ olefin |  | 1.8 |
| n-$C_{12}$ paraffin |  | 27.8 |
| n-$C_{12}$ olefin |  | 2.6 |
| n-$C_{13}$ paraffin |  | 22.6 |
| n-$C_{13}$ olefin |  | 2.7 |
| n-$C_{14}$ paraffin |  | 12.1 |
| n-$C_{14}$ olefin |  | 1.7 |
| n-$C_{15}$ paraffin |  | 0.4 |
| Total non-normals |  | 3.3 |
|  | TOTAL | 100.0 |
| Total non-normals |  | 3.3 |
| Total normal olefins |  | 8.8 |
| Total normal paraffins |  | 87.9 |
|  | TOTAL | 100.0 |
|  |  | Vol. % |
| Total olefins |  | 9.8 |
| Light ends |  | 0.2 |
| Total paraffins |  | 86.5 |
| Total non-normals |  | 3.5 |
|  | TOTAL | 100.0 |

The 3.5 volume percent non-normals in the above analysis are primarily aromatics. Another possible charge stock for the process would be a selected fraction from a gasoline produced by a fluid catalytic cracking unit. A typical analysis, from a 95° C. cut of such gasoline is as follows:

|  | Vol. % |
|---|---|
| Olefins | 25.4 |
| Paraffins and naphthenes | 72.3 |
| Aromatics | 2.3 |
|  | 100.0 |

To separate olefins from a feed mixture comprising olefins and saturates the feed mixture is contacted with one or more beds of the adsorbent and the olefins are more selectively adsorbed and retained by the adsorbent while the less selectively adsorbed saturates are removed from the interstitial void spaces between the particles of adsorbent and the surface of the adsorbent. The adsorbent containing the more selectively adsorbed olefins is referred as a "rich" adsorbent — rich in the more selectively adsorbed olefins.

The more selectively adsorbed feed components are commonly referred to as the extract components of the feed mixture, while the less selectively adsorbed components are referred to as the raffinate components. Fluid streams leaving the adsorbent comprising an extract component and comprising a raffinate component are referred to, respectively, as the extract stream and the raffinate stream. Thus, the raffinate stream will contain as raffinate components essentially all of the feed saturates and the extract stream will contain essentially all of the feed olefins as the extract components.

Although it is possible by the process of this invention to produce high purity (98% or greater), olefins at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of extract components and raffinate components both appearing in the particular stream. For example, the ratio of concentration of the more selectively adsorbed feed olefins to the concentration of less selectively adsorbed feed saturates will be highest in the extract stream, next highest in the feed mixture, and lowest in the raffinate stream. Likewise, the ratio of the concentration of the less selectively adsorbed feed saturates to the more selectively adsorbed feed olefins will be highest in the raffinate stream, next highest in the feed mixture, and the lowest in the extract stream.

The adsorbent can be contained in one or more chambers where through programed flow into and out of the chambers separation of the olefins is effected. The adsorbent may be contacted with a desorbent material which is capable of displacing the adsorbed olefins from the adsorbent. Alternatively, the olefins could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and a desorbent material (hereinafter described). In the simplest embodiment of the invention the adsorbent is employed in the form of a single static bed in which case the process is only semi-continuous. A set of two or more static beds may be employed in fixed-bed contacting with appropriate valving so that the feed mixture is passed through one or more adsorbent beds while the desorbent material is passed through one or more adsorbent beds while the desorbent material is passed through one or more of the other beds in the set. The flow of feed mixture and desorbent material may be either up or down through the adsorbent. Any of the conventional apparatus employed in static bed fluid-solid contacting may be used.

Countercurrent moving-bed or simulated moving-bed countercurrent flow systems, however, have a much greater separation efficiency than fixed adsorbent bed systems and are therefore preferred. In the moving-bed or simulated moving bed processes the adsorption and desorption operations are continuously taking place which allows both continuous production of an extract and a raffinate stream and the continual use of feed and desorbent streams. One preferred processing flow scheme which can be utilized to effect the process of this invention includes what is known in the art as the simulated moving-bed countercurrent flow system. The operating principles and sequence of such a flow system are described in U.S. Pat. No. 2,985,589 issued to D. B. Broughton. In such a system is is the progressive movement of multiple liquid access points down an adsorbent chamber that simulates the upward movement of adsorbent contained in the chamber. Only four of the access lines are active at any one time; the feed in, desorbent in, raffinate stream out, and extract stream out access lines. Coincident with this simulated upward movement of the solid adsorbent is the movement of the liquid occupying the void volume of the packed bed of adsorbent. So that countercurrent contact is maintained, a liquid flow down the adsorbent chamber is provided by a pump. As an active liquid access point moves through a cycle, that is, from the top of the chamber to the bottom, the chamber circulation pump moves through different zones which require different flow rates. A programmed flow controller is provided to set and regulate these flow rates.

The active liquid access points effectively divided the adsorbent chamber into separate zones, each of which has a different function. Zone 1, bounded by the feed in and raffinate stream out access points is the adsorption zone. The adsorbent entering this zone at the raffinate out access point contains only the raffinate components and desorbent. As it rises and contacts the descending liquid which is richer in the extract components, the selectivity of the adsorbent for the extract components causes them to be adsorbed. The displaced desorbent and raffinate components are withdrawn as the raffinate stream. The adsorbent leaving the zone at the feed in access point contains all of the adsorbed species. Zone 2, bounded by the feed in and extract stream out access points, is the rectification zone. The descending liquid entering this zone, being rich in extract components and desorbent, causes the replacement of the raffinate components from the ascending adsorbent. Zone 3, bounded by the extract out and desorbent in access points, is the desorption zone. The rising adsorbent from Zone 2, containing extract components and desorbent, is contacted by the descending desorbent stream, resulting in the desorption of the extract components. The exiting extract stream contains both desorbent and extract components. Zone 4, a secondary rectification zone, is bounded by the raffinate out and desorbent in access points. Here, desorbent from the ascending adsorbent is desorbed by the raffinate components in the liquid from Zone 1. The desorbent reclaimed reduces the quantity of external desorbent required to desorb the extract components in Zone 3. Fractionators are used to separate the extract and raffinate components from the desorbent in the extract and raffinate streams. More specifically, the simulated moving-bed countercurrent flow system is employed in one embodiment of the olefin separation process described in U.S. Pat. No. 3,510,423 issued to R. W. Neuzil et al. In a preferred embodiment our process is an improved process of that described in the Neuzil et al. patent.

Adsorption and desorption conditions for adsorptive separation processes can generally be either in the liquid or vapor phase or both but for aromatic isomer separation processes employing zeolitic adsorbents and the flow system described all liquid-phase operations are usually preferred. Preferred adsorption conditions for the process of this invention will include temperatures within the range of from about 70° F. to about 450° F. and will include pressures in the range from about atmospheric to about 500 psig. Pressures higher than about 500 psig. do not appear to affect the selectivity to a measurable amount and additionally would increase the cost of the process. Desorption conditions for the process of the invention shall generally include the same range of temperatures and pressures as described for adsorption operations. The desorption of the extract components could also be effected at subatmospheric pressures or elevated temperatures or both or by vacuum purging of the adsorbent to remove the extract components.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which a selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent.

However, in adsorptive separation processes which employ zeolitic adsorbents and which are generally operated at substantially constant pressures and temperatures to insure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Secondly, desorbent materials must be compatible with the particular adsorbent and the particular feed mixture. More specifically, they must not reduce or destroy the critical selectivity of the adsorbent for the extract components with respect to the raffinate component.

Desorbent materials to be used in the process of this invention should additionally be substances which are easily separable from the feed mixture that is passed into the process. After desorbing the extract components of the feed, both desorbent material and the extract components are removed in admixture from the adsorbent. Likewise, the raffinate components are withdrawn from the adsorbent in admixture with desorbent material. Without a method of separating desorbent material, such as distillation, the purity of neither the extract components nor the raffinate component would not be very high. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

In the preferred isothermal, isobaric, liquid-phase operation of the process of this invention, desorbent materials comprising olefins are particularly effective and preferred. Specifically, desorbent materials comprising straight-chain and branched-chain olefins having average boiling points substantially different from the feed mixture and having selectivites (hereinafter discussed in more detail) with respect to the feed olefins of about 1.0 are particularly preferred.

Mixtures of olefins with paraffins have, additionally, been found to be effective desorbent materials. The paraffins can include straight- or branched-chain paraffins or cycloparaffins having a boiling point substantially different from the feed to allow separation from feed components. Typical concentration of olefins used in admixture with a paraffin can be from a few volume percent up to near 100 vol.% of the total desorbent material and preferably will be within the range of from about 25 vol.% to about 100 vol.% with an even more preferred range being from about 50 vol.% to about 100 vol.% of the total desorbent material.

With the operation of our process now in mind, one can appreciate that certain characteristics of adsorbents are highly desirable, if not absolutely necessary, to the successful operation of the selective adsorptive process. Among such characteristics are: adsorptive capacity for some volume of desired olefins per volume of adsorbent; reduced or eliminated catalytic activity for undesired side reactions such as polymerizaton and isomerization; and selectivity of adsorption both for the feed olefins and the desorbent material with respect to the undesired feed components.

Capacity of the adsorbent for adsorbing a specific volume of olefins is, of course, a necessity; without such capacity the adsorbent is useless for adsorptive separation. Furthermore, the higher the adsorbent's capacity for the species to be adsorbed, the better is the adsorbent. Increased capacity of a particular adsorbent makes it possible to reduce the amount of adsorbent needed to separate the desired species contained in a particular rate of hydrocarbon feed mixture. A reduction in the amount of adsorbent required for a specific adsorptive separation reduces the cost of the separation process. It is important that the good initial capacity of the adsorbent be maintained during actual use in the separation process over some economically desirable life. For this reason, and others, it is necessary that the adsorbent possess little or no catalytic activity which would produce products that might degrade adsorbent capacity or selectivity.

It is additionally important that the highly reactive olefins are not reacted into side products which either degrade the product quality or reduce the overall yield of concentrated olefins. Where the feed stream to the process includes both normal and isomeric olefin hydrocarbons, the isomerization activity of the adsorbent is not of as much significance as the polymerization activity of an adsorbent. The polymerization of feed olefins by the adsorbent reduces the yield of olefinic hydrocarbon product and also degrades the adsorbent. The polymer produced destroys the effectiveness of the adsorbent by plugging up the surface of the adsorbent and the pores present in the structure of the adsorbent. This shortens the useful life of the adsorbent and makes necessary frequent regeneration treatments to restore the adsorptive properties of the adsorbent. In instances where one or more particular olefin isomers are desired to be separated and recovered in high purity from a feed stream which contains the isomers and saturates, the isomerization activity of the adsorbent becomes an equal if not greater problem than the polymerization activity. If the adsorbent possesses isomerization activity the product may be contaminated with undesired isomeric olefins produced from the feed olefins by the adsorbent.

Since both reactions seem to occur at the same time, the term "catalytic activity" as used herein shall mean both isomerization and polymerization activity. While reducing the temperature of the operations of the adsorption process in which the catalytic activity is present will substantially reduce the catalytic activity because of the associated reduction in the rate of reaction, this procedure in adsorptive separation processes employing molecular sieves, in most cases, is not desirable because the reduction in temperature also reduces the kinetic energy of the material passing into and out of the adsorbent. This substantially reduces the rate of exchange of feed olefins into and out of the adsorbent giving what is considered in the art as poor breakthrough fronts which results in product contamination with feed stock and relatively high requirements of adsorbent for a given throughput of olefin-containing feed stock. It is, therefore, extremely important that the catalytic activity be substantially reduced or preferably totally eliminated by proper methods of manufacture of a selected adsorbent.

The other important adsorbent characteristic is the ability of the adsorbent to separate components of the feed; or, in other words, the relative selectivity, (B), of the adsorbent for one component as compared to another component. Relative selectivity is expressed not only for the desired hydrocarbon type (olefins) as compared to undesired hydrocarbons but is also expressed between homologs of the desired hydrocarbon type. The relative selectivity (B) as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U}$$

where $C$ and $D$ are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where the selectivity of two components approaches 1.0 there is no preferential adsorption of one component by the adsorbent with respect to the other; they are both adsorbed (or non-adsorbed) to about the same degree. As the (B) becomes less than or greater than 1.0 there is a preferential selectivity by the adsorbent of one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. For optimum performance desorbants should have a selectivity equal to about 1 or slightly less than 1 with respect to all extract components so that all of the extract components can be extracted as a class and all raffinate components clearly rejected into the raffinate stream.

The adsorbent produced by the method of this invention has good capacity and selectivity for olefins and little or no catalytic activity thereby making it particularly effective for use in a process for the separation of olefins.

In order to test various adsorbents to measure the characteristics of adsorptive capacity, selectivity, and degree of catalytic activity, a dynamic testing apparatus was employed. The apparatus used consisted of an adsorbent chamber of approximately 40 cc. volume having inlet and outlet portions at opposite ends of the chamber. The chamber was contained within a temperature control means and, in addition, pressure control equipment was used to operate the chamber at a constant predetermined pressure. Attached to the outlet line of the chamber was chromatographic analysis equipment which was used to analyze the effluent stream leaving the adsorbent chamber.

The actual operations used to determine the adsorbent capacity were as follows. A feed mixture containing at least one adsorbable component in a dilute component was passed through the adsorbent bed until the effluent stream leaving the adsorbent chamber, as measured by the chromatograph, was essentially the same composition as the feed stream passing into the inlet of the adsorbent chamber. Generally, the adsorbable component used in the feed mixture is decene-1. This indicates that the sieve has reached equilibrium, that is, the adsorbent was no longer adsorbing materials from the external phase and that there was no longer a net transfer of the material between the adsorbed phase and the external phase.

A desorbent mixture, containing an adsorbable component different from that of the feed, in a diluent component, was then passed into the adsorbent chamber at conditions to effect desorption of the previously adsorbed feed mixture component. Octene-1 is usually used as the adsorbable component in the desorbent mixture. The desorbent mixture was continuously passed into the adsorbent chamber until the effluent material, as monitored by the chromatographic equipment was substantially identical to the desorbent feed material, indicating that equilibrium conditions had been achieved. Knowing the flow rate to the chamber and the effluent composition as continuously monitored by the chromatograph, the total amount of the components adsorbed by the adsorbent from the desorbent mixture can be calculated.

In order to determine the adsorptive capacity of the sieve for components in the feed mixture, the inlet stream to the chamber was then switched from the desorbent mixture back to the feed mixture to allow feed components to displace the previously adsorbed components from the desorbent mixtures. Again using the chromatograph and knowing the flow rate and effluent composition, the volume of feed components adsorbed can be calculated.

Selectivity can then be calculated using the previously mentioned equation for selectivity and the capacities determined above.

In measuring the polymerization activity of the type X adsorbent, the same gas chromatographic equipment and testing apparatus was used. Two variations of the polymerization test can be used. In the first variation, the degree of catalytic activity may be measured by the loss of a known concentration of feed olefin as detected in the effluent stream by the chromatographic equipment. The measure of polymerization is then an indirect determination, being related to the difference between the inlet and outlet olefin concentrations. This catalytic activity is thought to be primarily due to polymerization reactions of the feed olefins with a small part of the feed olefins that are isomerized to other internal olefinic isomers. The relative activity scale used to express the catalytic activity of the adsorbent is determined by measuring the peak height on the chromatograph equivalent to the inlet concentration of olefin as indicative of a zero catalytic activity. Hence, if the peak height of the olefins in the effluent is same as the peak height of a known concentration of olefins present in the feed the relative adsorbent activity is zero. An effluent peak height equal to one-half that of the feed would represent exactly 50% polymerization or isomerization of the feed olefin component. The adsorbent activity would therefore be 50%. Equation 2 below represents the formula used to determine catalytic activity of an adsorbent knowing the peak height of the olefins remaining in the effluent stream leaving the adsorbent chamber and the peak height of the olefins present in the feed.

$$\text{Adsorbent Activity} = 100 - 100 \frac{(Pe)}{(Pf)}$$

where $Pe$ represents the peak height of the effluent olefins and $Pf$ represents the peak height of the feed olefins.

The second variation of the catalytic activity test is to measure the polymer formed directly in the effluent stream with the chromatographic equipment. This method depends upon selecting a feed olefin, such as diisobutylene, that easily forms an identifiable polymer. The dimer peak height above the base line is then used as the measure of polymerization and catalytic activity is reported as dimer units. The first variation is particularly useful to initially determine the catalytic activity of various adsorbents while the second variation is particularly useful in more accurately determining catalytic activity of adsorbents shown by the first test variation to have low catalytic activity.

To translate this type of adsorbent capacity, selectivity, and activity data into actual olefin separation process performance requires actual testing of the adsorbent with various feed mixtures and desorbent materials in a countercurrent liquid-solid contacting device. The general operating principles of such a device has been previously described and are found in Broughton U.S. Pat. No. 2,985,589. A specific laboratory-size apparatus utilizing these principles is described in deRosset et al. U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are being withdrawn through two more. All remaining access lines are inactive and when the position of the distributing valve is advanced by one index, all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous, and D. H. Rosback presented at the American Chemical Society, Los Angeles, California, Mar. 28 through Apr. 2, 1971.

The improvement in the olefin separation process that resulted from employing the adsorbent prepared as described herein was confirmed by continuous testing in the laboratory-sized apparatus described above.

Adsorbents used in this process will comprise specific crystalline aluminosilicates or molecular sieves. Particular crystalline alumino-silicates include those having cage structures in which alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as molecular sieves. While separations with molecular sieves are commonly thought to occur because of differences in the sizes of molecules and while this may be true of some separations, such as the separation of normal paraffins from isoparaffins, the adsorptive separation of olefins from saturates takes place because of differences in electrochemical forces between olefins and saturates and the adsorbent rather than by pure physical size differences between the feed molecules.

In hydrated form, the crystalline aluminosilicates generally encompass those zeolites represented by the Formula 1 below:

Formula 1

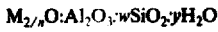

$$M_{2/n}O:Al_2O_3:wSiO_2:yH_2O$$

where M is a cation which balances the electrovalence of the tetrahedra and is generally referred to as an exchangeable cationic site, $n$ represents the valence of the cation, $w$ represents the moles of $SiO_2$, and $y$ represents the moles of water. The generalized cation M may be one or more of many possible cations.

The prior art has generally recognized that adsorbents comprising the type X and the type Y zeolites can be used in certain adsorptive separation processes. These zeolites are described and defined in U.S. Pat. Nos. 2,882,244 and 3,120,007 respectively. The terms "type X" and "type Y" zeolites as used herein shall include all zeolites which have general structures as represented in the above two cited patents.

The type X zeolite in the hydrated or partially hydrated form can be represented in terms of mole oxides as shown in Formula 2 below:

Formula 2

$$(0.9\pm0.2)M_{2/n}O:Al_2O_3:(2.5\pm0.5)SiO_2:yH_2O$$

where M represents at least one cation having a valence of not more than 3, $n$ represents the valence of M, and $y$ is a value up to about 9 depending upon the intensity of M and the degree of hydration of the crystal. As noted from Formula 2 the $SiO_2/Al_2O_3$ mole ratio for the type X zeolite is 2.5±0.5. The cation M may be one or more of a number of cations such as the hydrogen cation, the alkali metal cation, or the alkaline earth cations, or other selected cations, and is generally referred to as an exchangeable cationic site. As the type X zeolite is initially prepared, the cation M is usually predominately sodium and the zeolite is therefore referred to as a sodium-type X zeolite. Depending upon the purity of the reactants used to make the zeolite, other cations mentioned above may be present, however, as impurities.

The type Y zeolite in the hydrated or partially hydrated form can be similarly represented in terms of mole oxides as in Formula 3 below:

Formula 3

$$(0.9\pm0.2)M_{2/n}O:Al_2O_3:wSiO_2:yH_2O$$

where M is at least one cation having a valence not more than 3, $n$ represents the valence of M, $w$ is a value greater than about 3 up to 8, and $y$ is a value up to about 9 depending upon the intensity of M, and the degree of hydration of the crystal. The $SiO_2/Al_2O_3$ mole ratio for type Y zeolites can thus be from about 3 to about 8. Like the type X zeolite, the cation M may be one or more of a variety of cations but, as the type Y zeolite is initially prepared, the cation M is usually predominately sodium with the other cations present usually as impurities. The type Y zeolite containing predominately sodium cations at the exchangeable cationic sites is therefore referred to as a sodium-type Y zeolite.

The starting material which is used to make the adsorbent for our process is referred to in this specification as a precursor mass and comprises type X or type Y zeolites and a portion of amorphous material. The crystalline aluminosilicate material can be present in concentrations ranging from about 80% to about 98% of the weight of the precursor mass based on volatile free composition. Volatile free compositions are generally determined after the precursor mass has been calcined at 900° C. in order to drive off all volatile matter. The remaining material in the precursor mass generally comprises amorphous silica or alumina or both which is present in intimate mixture with the small particles of the zeolite material. This amorphous material may be an adjunct of the manufacturing process for the type X or type Y zeolite (for example, intentionally incomplete purification of either zeolite during its manufacture) or it may be added to relatively pure type X zeolite to aid in extrusion or pelleting of the zeolite. Normally the precursor mass whether in the extrudate or pellet form is first granulated to a particle size range of about 16–40 mesh (Standard U.S. Mesh) before the caustic treatment step is begun. This is approximately the desired particle size of the finished adsorbent.

The caustic treatment step is primarily an ion exchange step in which sodium cations replace non-sodium cation impurities in the zeolite-containing precursor mass thereby reducing or eliminating the catalytic activity of the zeolite. Although mild ion exchange conditions are employed, this step additionally removes a small amount of silica or silica and alumina thereby increasing the capacity of the material for olefins. Total silica and alumina removal from the precursor mass is from about 1 to about 15% and is generally in the range of 5 to 15%. Further evidence of this is the increase in the percent zeolite, (as determined by X-ray analysis) and surface area and also the slight reduction in the $SiO_2/Al_2O_3$ ratio of the starting material. The silica or silica and alumina removed is thought to be primarily a portion of the amorphous binder whether silica or alumina or both, in the precursor mass, as evidenced by the closer agreement of the $SiO_2/Al_2O_3$ ratio of the finished adsorbent as determined by both chemical analysis and by X-ray.

We have found not only that this ion exchange step significantly reduces catalytic activity but specifically that the amount of activity reduction isproportional to the amount of sodium cation contained by the finished adsorbent. This relationship, with the amount of sodium expressed as the ratio $Na_2O/Al_2O_3$, is indicated in Table 2 below. Catalytic activities for a particular precursor mass comprising 13X molecular sieves and for various adsorbents prepared from the precursor mass were determined using the more sensitive of the activity tests previously described.

Table 2

| Relationship Between $Na_2O/Al_2O_3$ and Catalytic Activity | | |
| --- | --- | --- |
| Adsorbent | $Na_2O/Al_2O_3$ | Catalytic Activity (Dimer Units) |
| Precursor mass | .61 | 55 |
| A | .78 | 4.5 |
| B | .81 | 3.75 |
| C | .83 | 2.35 |
| D | .85 | 2.05 |
| E | .88 | 1.10 |
| F | .91 | 0 |

As shown in the table, catalytic activity decreases with increasing sodium ion content from an unacceptable 55 dimer units of the precursor mass to about zero as the $Na_2O/Al_2O_3$ ratio approaches 1. For an acceptable adsorbent it is preferred that the $Na_2O/Al_2O_3$ ratio of the final product be greater than about 0.70.

Ion exchange conditions should be so regulated to achieve this desired degree of ion exchange. The degree of ion exchange achieved is a function of the three variables of caustic concentration, temperature at which the ion exchange is conducted, and the length of time the ion exchange is continued. The ion exchange solutions employed herein are preferably water solutions of sodium hydroxide. Suitable concentrations to obtain the desired ion exchange can be from about 0.5 to 10% by weight of sodium hydroxide with the preferred concentration being from about 0.5 to 5% by weight. By using solutions of these concentrations, the desired ion exchange can be obtained at temperatures from about 50° to 300° F. with temperature from about 150° to 250° F. being preferred. Operating pressure is not critical and need only be sufficient to insure a liquid phase. Operating pressures can range from about atmospheric pressure to about 100 psig. The length of time required for the ion exchange will vary depending upon the solution concentration and temperatures from about 0.5 to 5 hours. At the above preferred concentration and temperatures, a contact time which has been shown to be specifically preferred is about 2 to 3 hours. The ion exchange step should be controlled so that the zeolite structure will not be destroyed and so that the final product will have a $Na_2O/Al_2O_3$ ratio greater than about 0.7. Periodic sampling and analyses can be employed if desired to closely monitor the progress of this step.

The next step in the manufacture of the adsorbent is the washing step for the purpose of removing excess sodium hydroxide solution remaining within the ion-exchanged adsorbent mass. The washing medium is water which has a pH greater than 7 and preferably within the range of 7 to about 10. If necessary the water is adjusted to and maintained at the desired pH by adding a small amount of sodium hydroxide solution. Since the primary purpose of the ion exchange was to remove hydrogen cation (and metal cation) contaminates, this pH range is necessary to avoid redepositing hydrogen cation on the adsorbent mass. Washing temperatures can include temperatures within the range of about 100° F. to about 200° F. with a temperature of 135° F. to 145° F. preferred. Although the washing step can be done in a batch manner with one aliquot of wash water at a time, the washing step is generally and preferably done on a continuous flow type basis with water passed through a bed of the adsorbent at a given liquid hourly space velocity and a temperature for a period of time in order that from about 1 to about 5 gallons of water per pound of starting material is used to wash the material. Preferred washing conditions include using liquid hourly space velocities from about 0.5 to about 5, with 1.5 being preferred, to pass from about 1 to about 3 gallons of wash water per pound of starting material over the ion exchanges adsorbent. A good indication of complete washing is made by measuring the pH of the effluent wash water and comparing it to the pH of the fresh feed wash water. When they are the same, washing can generally be considered as complete.

When the wash step is completed the wet adsorbent particles will usually contain from about 30 to about 50 wt.% volation matter (water) as measured by loss on ignition (L.O.I.) at 900° C. The remaining step in the method of manufacture then is the drying step in which the volatile content of the washed adsorbent is reduced to less than about 10 wt.% L.O.I. at 900° C. with the preferred volatile content being about 5 to 7 wt.% L.O.I. at 900° C. Drying conditions include the presence of air and can include temperature from about 100° F. to about 100° F. The time required to achieve the desired volatile content will vary depending upon the drying temperature and the exact volatile content of the water-washed adsorbent particles to be dried.

The following is presented to illustrate the improved properties of the adsorbent to be used in our process and is not intended to unduly limit the scope of the appended claims.

EXAMPLE

An adsorbent, comprising sodium type X zeolite and having improved capacity for olefins and acceptably low catalytic activity, was produced using the following procedure.

A precursor mass comprising commercially available 13× molecular sieves and amorphous binder in the form of nominal 1/16-inch extrudate obtained from Union Carbide Linde Division, was ground to produce 16–40 U.S. Standard mesh particle size material having physical and chemical properties as shown in Table No. 3 shown below. Olefin capacity and catalytic activity were obtained using the testing apparatus and procedures previously described.

Table 3

| Properties of the Precursor Mass |
| --- |
| Chemical Properties |

Table 3-continued

| Properties of the Precursor Mass | |
|---|---|
| Volatile Matter (loss on ignition at 900° C.), wt. % | 3.2 |
| $SiO_2$ (volatile free) wt. % | 50.7 |
| $Al_2O_3$ (volatile free) wt. % | 33.6 |
| $Na_2O$ (volatile free) wt. % | 12.4 |
| $Na_2O/Al_2O_3$ | .61 |
| $SiO_2/Al_2O_3$ | 2.56 |
| Physical Properties | |
| Apparent Bulk Density, gm/cc | 0.635 |
| Surface Area, $M^2$/gm | 500 |
| Pore Volume, ml/gm | 0.30 |
| Pore Diameter, A | 24 |
| Area % faujasite (X-ray) | 93 |
| $SiO_2/Al_2O_3$ (X-ray) | 2.5 |
| Particle size distribution: | |
|   | 0.3 |
| on 20 | 33.3 |
| on 30 | 37.9 |
| on 40 | 21.4 |
| on 56 | 6.1 |
| on 60 | 0.3 |
| through 60 U.S. Screen | 0.7 |
| Testing Data | |
| $A_8$, cc of octene-1/40cc adsorbent | 3.1 |
| $A_{10}$, cc of decene-1/40cc adsorbent | 2.8 |
| Catalytic Activity, Dimer Units | 55 |

One hundred pounds of the granular precursor mass was loaded into an ion exchange tower against an upward flow of 1.6 wt.% NaOH solution at a rate such that the effluent temperature did not exceed 145° F. After all of the material was loaded, the material was ion exchanged by passing the 1.6 wt.% NaOH solution upflow through the ion exchange tower at a liquid hourly space velocity (LHSV) of 1.5 and a temperature of 200° F. until a total of 0.335 pounds of NaOH per pound of volatile-free precursor mass had been passed through the tower.

After the ion exchange step the ion exchanged material was water washed by passing treated water, having a pH of 10, upflow through the tower at 1.5 LHSV and 140° F. to a total of 1.3 gallons of water per pound of volatile free starting material.

The washed material was then dewatered, unloaded from the ion exchange tower, and dried in a forced air oven at 570° F. to a volatile content of 5.0 wt.% LOI at 900° C. An overall yield of 72% dried 16-40 U.S. mesh granular adsorbent was obtained by this procedure. Properties of the finished adsorbent are shown in Table No. 4 below.

Table 4

| Properties of the Finished Adsorbent | |
|---|---|
| Chemical Properties | |
| Volatile Matter (loss on ignition at 900° C.) wt. % | 5.0 |
| $SiO_2$ (volatile free) wt. % | 48.0 |
| $Al_2O_3$ (volatile free) wt. % | 32.1 |
| $Na_2O$ (volatile free) wt. % | 15.8 |
| $Na_2O/Al_2O_3$ | 0.81 |
| $SiO_2/Al_2O_3$ | 2.54 |
| Physical Properties | |
| Apparent Bulk Density, gm/cc | 0.671 |
| Surface area, $M^2$/gm | 516 |
| Pore volume, ml/gm | 0.27 |
| Pore diameter, A | 110 |
| Area % faujasite (X-ray) | 110 |
| $SiO_2/Al_2O_3$ (X-ray) | 2.5 |
| Particle Size Distribution | |
| Wt. % on 16 U.S. Screen | 0.0 |
| on 20 | 22.7 |
| on 30 | 37.1 |
| on 40 | 29.0 |
| on 56 | 8.2 |
| on 60 | 0.1 |
| through 60 U.S. Screen | 2.9 |
| Testing Data | |
| Olefin Capacity: | |
| $A_8$, cc of octene-1/40cc adsorbent | 3.78 |
| $A_{10}$, cc of decene-1/40cc adsorbent | 3.35 |
| Catalytic Activity, Dimer Units | 3.9 |

Testing results shown in Tables 3 and 4 show that the adsorbent olefin capacity has been increased from 3.1 to 3.78 cc of octene-1 per 40 cc of adsorbent or about 22% and from 2.8 to 3.35 cc of decene-1 per 40 cc of adsorbent or about 20%. As importantly, the catalytic activity has been substantially decreased from 55 dimer units to an acceptable activity 3.9 dimer units. The $Na_2O$ content of the adsorbent has been increased about 25% from 12.4 wt.% $Na_2O$ ($Na_2O/Al_2O_3$ of 0.61) for the precursor mass to 15.8 wt.% $Na_2O$ ($Na_2O/Al_2O_3$ of 0.81) for the finished adsorbent with less than about 15% reduction each in the $SiO_2$ and $Al_2O_3$ content.

We claim as our invention:

1. In a process for the separation of olefins from a feed mixture comprisng olefins and saturates which process comprises the steps of:
   a. contacting at adsorption conditions said mixture with an adsorbent comprising sodium type Y zeolite; and,
   b. selectively adsorbing said olefins to the substantial exclusion of said saturates and thereafter recovering said olefins, the improvement which comprises employing an adsorbent prepared by the steps of:
   i. contacting a precursor mass comprising a type Y zeolite having a $Na_2O/al_2O_3$ ratio less then about 0.7 with an aqueous sodium hydroxide solution having a sodium hydroxide cencentration of from about 0.5 to 10% by weight at a temperature of from about 50° to 300° F. for a time period of from about 0.5 to 5 hours to increase the sodium cation content to a $Na_2O/Al_2O_3$ ratio of greater than about 0.7 and to remove from about 1 to about 15 wt.% silica and alumina from the precursor mass;
   ii. washing said mass with water maintained at pH greater than 7 to remove excess sodium hydroxide solution and,
   iii. at least partially dehydrating said mass at dehydrating conditions.

2. The process of claim 1 further characterized in that said olefins have from about 4 to about 25 carbon atoms per molecule.

3. The process of claim 1 further characterized in that said adsorption conditions are selected from a temperature within the range of from about 70° F. to about 450° F. and a pressure within the range of from about atmospheric to about 500 psig.

4. The process of claim 1 including the step of treating the adsorbent containing the adsorbent olefins with a desorbent material to remove adsorbed olefins therefrom as a fluid extract stream.

5. In a process for the separation of olefins from a feed mixture comprising olefins and saturates which process comprises the steps of:
   a. contacting said feed mixture with an adsorbent comprising a sodium type Y zeolite at adsorption conditions to effect the selective adsorption of said olefins by said adsorbent;
   b. withdrawing from said bed of adsorbent a reffinate stream comprising less selectively adsorbed saturates;
   c. contacting the adsorbent bed with a desorbent material at desorption conditions to effect desorption of said olefins from said adsorbent; and,
   d. withdrawing a stream containing olefins and desorbent material from said bed of adsorbent;

the improvement which comprises employing a zeolite adsorbent prepared by the steps of:
  i. contacting a precursor mass comprising a type Y zeolite having a $Na_2O/Al_2O_3$ ratio of less than about 0.7 with an aqueous sodium hydroxide solution having a sodium hydroxide concentration of from about 0.5 to 10% by weight at a temperature of from about 50° to 300° F. for a time period of from about 0.5 to 5 hours to increase the sodium cation content to a $Na_2O/Al_2O_3$ ratio of greater than about 0.7 to remove from about 1 to about 15 wt.% silica and alumina from the precursor mass;
  ii. washing said mass with water maintained at a pH greater than 7 to remove excess sodium hydroxide; and,
  iii. at least partially dehydrating said mass at dehydrating conditions.

6. The process of claim 5 further characterized in that said olefins have from about 4 to about 25 carbon atoms per molecule.

7. The process of claim 5 further characterized in that said adsorption and desorption conditions include temperatures within the range of from about 70° F. to about 450° F. and pressures within the range of from about atmospheric to about 500 psig.

8. The process of claim 5 further characterized in that said adsorption and desorption conditions are effected in the liquid phase.

9. The process of claim 5 further characterized in that said desorption material has an average boiling point substantially different than that of the feed mixture.

10. The process of claim 9 further characterized in that said desorbent material comprises a straight chain olefin.

* * * * *